(12) United States Patent
Stien et al.

(10) Patent No.: US 8,876,848 B2
(45) Date of Patent: Nov. 4, 2014

(54) DILATOR AND ELONGATE GUIDE WIRE AND METHOD OF USING SAME

(75) Inventors: Karl E. Stien, Eau Claire, WI (US); Nathaniel J. Stewart, Eau Claire, WI (US)

(73) Assignee: Stewart and Stien Enterprises, LLC, Eau Claire, WI (US)

( * ) Notice: Subject to any disclaimer, the term of this patent is extended or adjusted under 35 U.S.C. 154(b) by 0 days.

(21) Appl. No.: 13/542,134

(22) Filed: Jul. 5, 2012

(65) Prior Publication Data
US 2013/0331880 A1 Dec. 12, 2013

Related U.S. Application Data

(60) Provisional application No. 61/656,048, filed on Jun. 6, 2012.

(51) Int. Cl.
  *A61B 17/14* (2006.01)
  *A61F 11/00* (2006.01)
  *A61M 5/00* (2006.01)

(52) U.S. Cl.
  USPC ............................ 606/184; 606/108; 604/264

(58) Field of Classification Search
  USPC ................. 600/184; 606/108, 434, 191, 190; 604/164.04
  See application file for complete search history.

(56) References Cited

U.S. PATENT DOCUMENTS

| | | | | |
|---|---|---|---|---|
| 4,364,391 A * | 12/1982 | Toye | ........................ | 128/207.29 |
| 4,884,579 A * | 12/1989 | Engelson | ...................... | 600/585 |
| 5,057,083 A * | 10/1991 | Gellman | .................... | 604/164.1 |
| 5,058,580 A * | 10/1991 | Hazard | ..................... | 128/207.15 |
| 5,095,915 A * | 3/1992 | Engelson | ...................... | 600/585 |
| 5,465,733 A * | 11/1995 | Hinohara et al. | ............. | 600/585 |
| 5,474,535 A * | 12/1995 | Place et al. | ...................... | 604/60 |
| 5,773,020 A * | 6/1998 | Place et al. | ..................... | 424/426 |
| 5,865,826 A * | 2/1999 | Paul | ................................. | 606/1 |
| 5,885,217 A * | 3/1999 | Gisselberg et al. | ........... | 600/434 |
| 5,910,134 A * | 6/1999 | Fussman | .................. | 604/164.06 |
| 5,980,493 A * | 11/1999 | Smith et al. | ............. | 604/164.11 |
| 6,637,435 B2 * | 10/2003 | Ciaglia et al. | ............ | 128/207.29 |
| 6,695,850 B2 * | 2/2004 | Diaz | .............................. | 606/91 |
| 6,814,718 B2 * | 11/2004 | McGuckin et al. | ............. | 604/264 |
| 6,926,728 B2 * | 8/2005 | Zucherman et al. | .......... | 606/190 |
| 7,198,631 B2 * | 4/2007 | Kanner et al. | ................ | 606/139 |
| 7,306,574 B2 | 12/2007 | Massey et al. | | |
| 7,632,277 B2 * | 12/2009 | Woll et al. | .................... | 606/86 R |
| 7,695,489 B2 * | 4/2010 | Brockman | .................... | 606/197 |
| 7,713,193 B2 * | 5/2010 | Nance et al. | .................. | 600/184 |
| 7,776,062 B2 * | 8/2010 | Besselink et al. | ............. | 606/191 |
| 8,202,289 B2 * | 6/2012 | Woo | ............................... | 606/185 |
| 8,396,532 B2 * | 3/2013 | Jenkins et al. | ................ | 600/423 |
| 8,485,969 B2 * | 7/2013 | Grayzel et al. | ................ | 600/184 |
| 2002/0026207 A1 * | 2/2002 | Stellon et al. | ................. | 606/185 |

(Continued)

*Primary Examiner* — Tuan V Nguyen
*Assistant Examiner* — Chima Igboko
(74) *Attorney, Agent, or Firm* — Wood, Phillips, Katz, Clark & Mortimer

(57) ABSTRACT

The combination of a) a dilator having: a tubular body with a length, an internal passage, and proximal and distal ends spaced in a lengthwise direction; and b) an elongate guide wire having a length and capable of being received in, and movable in a lengthwise direction within, the internal passage with the dilator and guide wire in operative relationship. The tubular body has a locally flexible length that allows a limited predetermined degree of bending of the tubular body at, or adjacent, the distal end of the tubular body to allow the dilator to conform to a curved guide wire shape.

16 Claims, 4 Drawing Sheets

(56) References Cited

U.S. PATENT DOCUMENTS

| | | | |
|---|---|---|---|
| 2002/0133128 A1* | 9/2002 | Heller | 604/270 |
| 2004/0015138 A1* | 1/2004 | Currier et al. | 604/264 |
| 2004/0138589 A1* | 7/2004 | Egnelov et al. | 600/585 |
| 2004/0243212 A1* | 12/2004 | Dadd et al. | 607/137 |
| 2005/0131393 A1* | 6/2005 | Chu et al. | 606/1 |
| 2005/0216007 A1* | 9/2005 | Woll et al. | 606/62 |
| 2005/0234437 A1* | 10/2005 | Baxter et al. | 606/15 |
| 2006/0124134 A1* | 6/2006 | Wood | 128/207.29 |
| 2006/0208028 A1* | 9/2006 | Kanner | 227/175.1 |
| 2007/0060927 A1* | 3/2007 | Longson et al. | 606/108 |
| 2007/0156219 A1* | 7/2007 | Sommer et al. | 607/131 |
| 2008/0009797 A1* | 1/2008 | Stellon et al. | 604/164.08 |
| 2008/0009823 A1* | 1/2008 | McKay | 604/500 |
| 2008/0125791 A1* | 5/2008 | Gellman et al. | 606/108 |
| 2008/0146967 A1* | 6/2008 | Richardson et al. | 600/585 |
| 2009/0024089 A1 | 1/2009 | Levine et al. | |
| 2009/0209912 A1* | 8/2009 | Keyser et al. | 604/164.1 |
| 2009/0216238 A1* | 8/2009 | Stark | 606/96 |
| 2009/0306657 A1* | 12/2009 | Piippo et al. | 606/45 |
| 2009/0312784 A1* | 12/2009 | Tupper | 606/191 |
| 2009/0318896 A1* | 12/2009 | Weststrate et al. | 604/533 |
| 2010/0010334 A1* | 1/2010 | Bleich et al. | 600/373 |
| 2010/0016984 A1* | 1/2010 | Trabish | 623/22.32 |
| 2010/0036226 A9* | 2/2010 | Marino et al. | 600/373 |
| 2010/0262158 A1* | 10/2010 | Siegel et al. | 606/108 |
| 2010/0298832 A1 | 11/2010 | Lau et al. | |
| 2011/0087234 A1* | 4/2011 | Ayala et al. | 606/108 |
| 2011/0166579 A1 | 7/2011 | Deem et al. | |
| 2011/0245800 A1* | 10/2011 | Kassab et al. | 604/506 |
| 2011/0275935 A1* | 11/2011 | Ginsburg et al. | 600/433 |
| 2011/0319898 A1* | 12/2011 | O'Neil et al. | 606/84 |
| 2012/0116323 A1* | 5/2012 | Moehle et al. | 604/264 |
| 2012/0123464 A1* | 5/2012 | Rasmussen et al. | 606/191 |
| 2012/0316565 A1* | 12/2012 | Stark | 606/80 |
| 2013/0255694 A1* | 10/2013 | Arlow et al. | 128/207.29 |

* cited by examiner

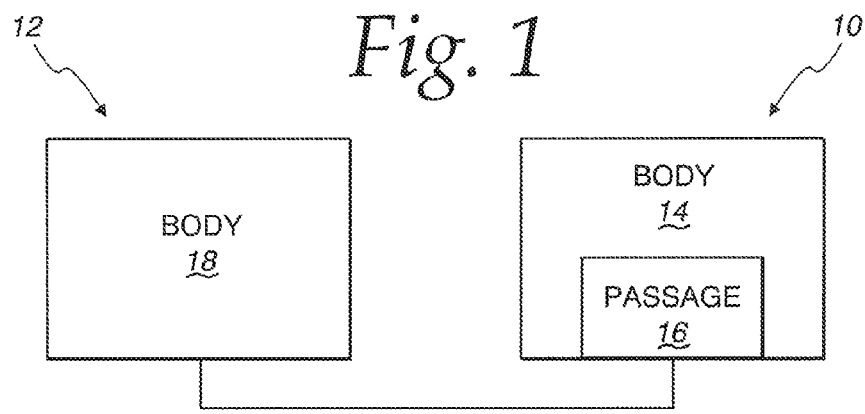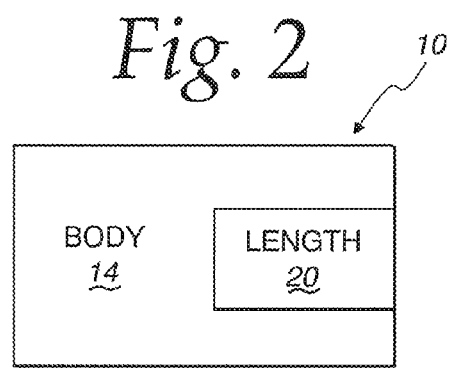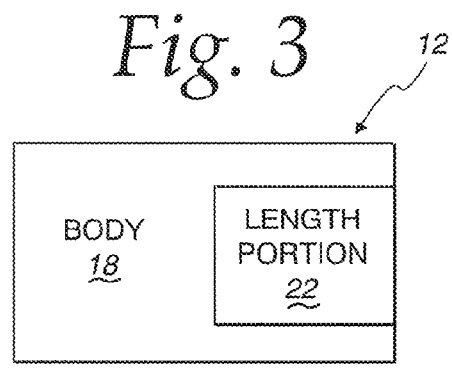

DILATOR AND ELONGATE GUIDE WIRE AND METHOD OF USING SAME

BACKGROUND OF THE INVENTION

CROSS-REFERENCE TO RELATED APPLICATIONS

This application is a non-provisional of U.S. Ser. No. 61/656,048 filed Jun. 6, 2012.

FIELD OF THE INVENTION

This invention relates to surgical instruments and, more particularly, to a dilator and an elongate guide wire usable to situate the dilator so that an instrument can be controllably advanced through the dilator to a site within a patient's body at which a procedure is to be performed.

BACKGROUND ART

It is known to perform arthroscopic joint surgery by retracting a patient's hip preparatory to advancing a needle into the femoral-acetabular joint space. Such retraction is often impractical. Among other concerns are: a) the potential for infliction of nerve damage; and b) situation of the femur at a less than desirable orientation for performance of a particular procedure. When adequate retraction has not been possible, alternative approaches have been utilized.

One alternative approach involves insertion of instrumentation down onto the femoral neck. While a viable alternative, this procedure has a number of potential limitations, primarily due to the structural and functional limitations of existing guide wires and dilators.

Notably, guide wires are made with a uniform, relatively stiff construction. As a result, it may be difficult to cause the guide wire to bend from a needle with the tip thereof on the cortex to advance into the joint along the femoral neck. As a result, the surgeon may encounter significant resistance.

Further, the dilator itself is generally stiffer than the guide wire, as a result of which it produces a localized stress on the bent wire as the dilator enters the fibrous capsule around the joint. As a result, there is a potential for the guide wire to kink or break under the forces imparted by the advancing dilator.

Generally, the existing technology for access needles, guide wires, and dilators is such that they are basically ineffective for facilitating arthroscopic surgery using the femoral neck access approach. To the extent that such components are utilized, a surgeon is often challenged to complete the process and commonly will take an undesirably long amount of time to complete a procedure.

SUMMARY OF THE INVENTION

In one form, the invention is directed to the combination of: a) a dilator having a tubular body with a length, an internal passage, and proximal and distal ends spaced in a lengthwise direction; and b) an elongate guide wire having a length and capable of being received in, and movable in a lengthwise direction within, the internal passage with the dilator and guide wire in operative relationship. The tubular body has a locally flexible length that allows a limited predetermined degree of bending of the tubular body at, or adjacent, the distal end of the tubular body to allow the dilator to conform to a curved guide wire shape.

In one form, the tubular body has a tapered length at the distal end of the tubular body.

In one form, the tapered length is in the range of 3-8 cm.

In one form, the tubular body is made from at least first and second different materials, with the first material being more flexible than the second material.

In one form, the tubular body has a tapered length at the distal end of the tubular body and at least a part of the tapered length is made from the first material.

In one form, the tapered length is in the range of 3-8 cm.

In one form, the part of the tapered length made from the first material has a length in the range of 2-6 cm.

In one form, the first material is rubber.

In one form, the second material is plastic.

In one form, the distal end of the dilator has a tip and a material that is less flexible than the second material makes up another part of the tapered length of the tubular body between the part of the tapered length made from the first material and the tip.

In one form, the material that makes up another part of the tapered length of the tubular body is plastic.

In one form, the material that makes up the another part of the tapered length is the second material.

In one form, the guide wire has a distal end and a body having a sleeve and a core surrounded by the sleeve and having a portion projecting from the sleeve. The projecting portion of the core defines a distal region of the guide wire that is locally more flexible than a portion of the guide wire where the sleeve surrounds the core.

In one form, the guide wire has varying flexibility over the length of the guide wire.

In one form, the guide wire has a distal end and the guide wire is more flexible at the distal end of the guide wire than at a location spaced from the distal end of the guide wire.

In one form, the guide wire has a progressively changing flexibility that increases toward the distal end of the guide wire.

In one form, the tubular body is made from at least first and second different materials, with the first material being more flexible than the second material.

In one form, the tubular body has a tapered length at the distal end of the tubular body and at least a part of the tapered length is made from the first material.

In one form, the invention is further directed to a method of placing a dilator in an operative position in a femoral-acetabular joint space. The method includes the steps of: providing the combination, as in claim 1 with the guide wire having a distal end; directing the distal end of the guide wire into the femoral-acetabular joint space in a manner whereby the guide wire has a bent length; and with the guide wire in the internal passage and spaced from the bent length of the guide wire, advancing the distal end of the dilator so that the locally flexible length of the tubular body engages and conforms to the bent length of the guide wire.

In one form, the guide wire has varying flexibility over the length of the guide wire.

In one form, the guide wire has a body with a sleeve and a core surrounded by the sleeve. A portion of the core projects from the sleeve and is more flexible than a portion of the guide wire where the sleeve surrounds the core. The bent length is defined by the projecting portion of the core.

BRIEF DESCRIPTION OF THE DRAWINGS

FIG. 1 is a schematic representation of a dilator and elongate guide wire, according to the invention, with the dilator and guide wire in operative relationship.

FIG. 2 is a schematic representation showing further detail of the dilator;

FIG. 3 is a schematic representation showing further detail of the guide wire;

DETAILED DESCRIPTION OF THE PREFERRED EMBODIMENT

Figure 4:
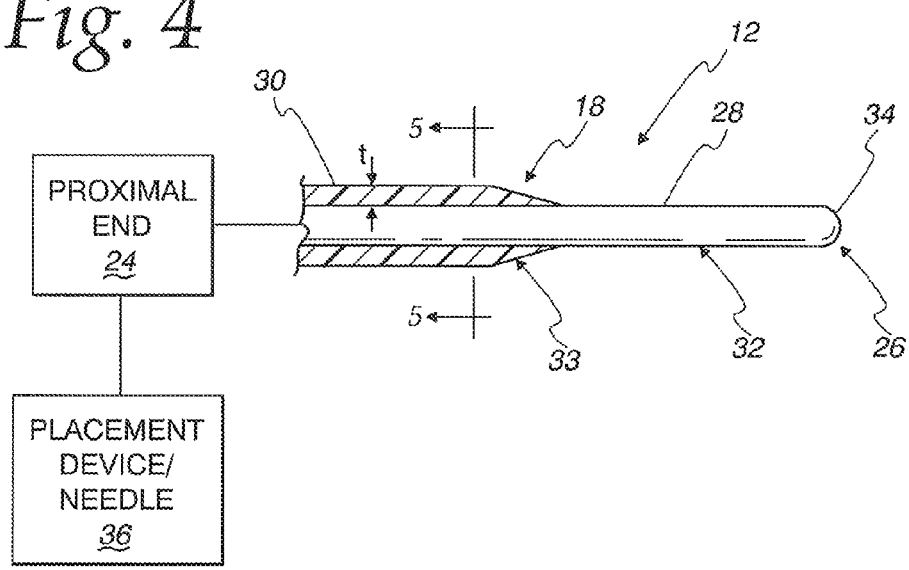
FIG. 4 is a partially schematic, side elevation view of a specific form of guide wire, according to the invention, with an associated placement device/needle.
Figure 5:
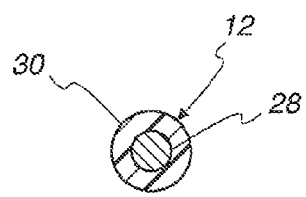
FIG. 5 is a cross-sectional view of the guide wire taken along line 5-5 of FIG. 4.
Figure 7:
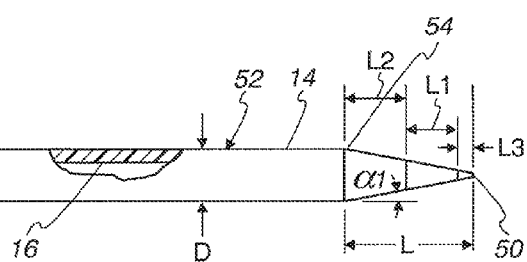
FIG. 7 is a partially schematic, elevation view of one specific form of dilator, as shown in FIGS. 1 and 2.

In FIG. 1, a dilator 10 and guide wire 12, according to the present invention, are shown in schematic form. The schematic showing of these components is intended to encompass specific embodiments described hereinbelow, as well as modifications thereto, which would be readily derivable by one skilled in the art with the teachings herein in hand.

The dilator 10 has a tubular body 14 with a length, an internal passage 16, and proximal and distal ends spaced in a lengthwise direction.

The guide wire 12 has a body 18 and a length capable of being received in, and movable in a lengthwise direction within, the dilator passage 16 with the dilator 10 and guide wire 12 in operative relationship.

As shown in FIG. 2, the body 14 of the dilator 10 has a locally flexible length 20 that allows a limited predetermined degree of bending of the body 14 at, or adjacent, the distal end of the body 14 to allow the dilator 10 to conform to the guide wire 12, when in a curved configuration.

As shown in FIG. 3, the body 18 of the guide wire 12 has a length portion 22 that is more flexible than another portion of the body 18. As explained below, the length portion 22 is preferably adjacent the distal end of the body 18, though this is not required. This length portion 22 may have a uniform flexibility or a flexibility that varies, as progressively in a lengthwise direction, potentially increasing in a direction toward a distal extremity.

Specific forms of the dilator 10 and guide wire 12 are shown in FIGS. 4-9. The elongate guide wire 12 has a proximal end 24 and a distal end 26 spaced from each other in a lengthwise direction. The guide wire body 18 is made up of a core 28 that is surrounded by a sleeve 30. A portion 32 of the core 28 projects from the sleeve 30 and defines a distal region of the guide wire 12 that is locally more flexible than that portion of the guide wire 12 where the sleeve 30 surrounds the core 28. The sleeve 30 tapers over a transition region at 33, that may extend lengthwise in an exemplary form over a length of 2-4 cm, and accounts for progressively varying flexibility between where the core 28 is exposed and where the full thickness t of the sleeve 30 surrounds the core 28. A tip 34 at the distal end 26 is blunted to avoid hangup as when the guide wire 12 is advanced by being pressed against a surface, particularly one which it encounters that requires the guide wire to change directions.

The core 28 of the guide wire 12 may be made from materials typically used in guide wire construction. The sleeve 30 may be made from a like material or another material that is metal or non-metal. As one possibility, the core 28 may be made from metal, with the sleeve 30 being made from a plastic or composite. The sleeve 30 rigidifies the core 28 and is preferably made from a relatively stiff material that bends less readily than the material defining the core 28. The structural interaction of the sleeve 30 and core 28 by itself rigidifies the body 18, even if the sleeve 30 and core 28 are made from the same material. With this construction, the core 28 and sleeve 30 cooperate to prevent failure of the sleeve 30 in the event that the sleeve 30 has large bending forces imparted thereto during insertion. The sleeve 30 thus performs rigidifying, bending control, and protective functions.

Figure 6:
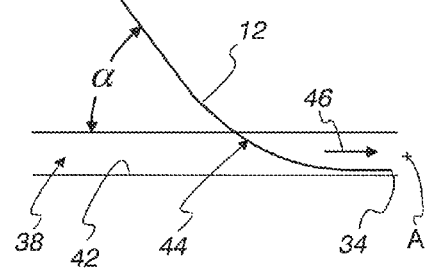
FIG. 6 is an elevation view of the inventive guide wire directed into a space so as to situate a distal end of the guide wire at an access location.

The guide wire 12 can be directed into a cavity/space using a conventional placement device/needle 36. FIG. 6 depicts the guide wire 12 directed into a bound space 38. As the guide wire 12 is advanced in a line, indicated by the arrow 40, at an angle α to its intended travel path within the space 38, the tip 34 contacts a surface 42 bounding the space 38 and deflects/bends. A bent portion 44 in this case remains in the vicinity of the site at which the guide wire 12 enters the space 38. This bending action allows the tip 34 to continue advancing through the space 38 in the direction of the arrow 46 to the desired access site A. The more flexible distal portion of the guide wire 12 facilitates initial advancement of the guide wire 12 to the access site A, using the placement device/needle 36.

Figure 8:
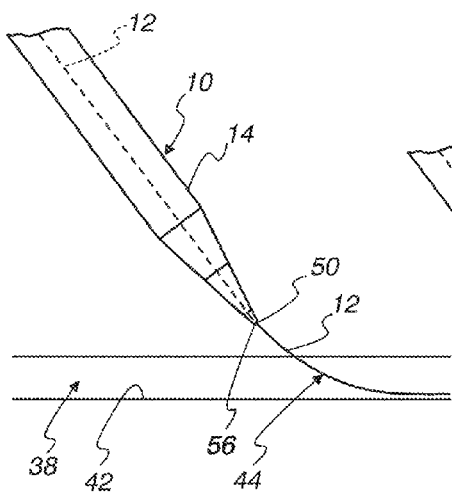
FIG. 8 is a view as in FIG. 6 with the dilator in FIG. 7 partially advanced over the guide wire.

Once the guide wire 12 is placed as in FIG. 6, the dilator 10 can be placed in operative relationship with the guide wire 12 and advanced in a lengthwise direction guidingly thereover, as shown in FIG. 8. The guide wire 12 resides within the dilator passage 16, with the guide wire 12 and dilator 10 in operative relationship, and guides lengthwise movement of the dilator 10.

In one embodiment, the guide wire 12 extends fully through the passage 16 and beyond each of proximal and distal ends 48, 50 of the dilator 10. As the distal end 50 of the dilator 10 moves up to the bent portion 44 of the guide wire 12, the dilator 10 is required to conformingly shape thereto so as to allow placement of the distal end 50 of the dilator 10 at the desired access site A. This bending is shown most clearly in FIG. 9.

To allow the contemplated controlled bending of the body 14, the dilator 10 is made as follows. The body 14 consists of a main length 52 extending from the proximal end 48 to a lengthwise location at 54 from where the diameter of the body 14 tapers progressively to the distal end 50. In this embodiment, the main length 52 has a diameter D that is substantially uniform. The main length 52 may be made from a plastic material that is relatively rigid, allowing a limited degree of bending under anticipated insertion forces. A tapered length L, between the location 54 and distal end 50, is made to be more flexible than the main length 52. In the embodiment depicted, the tapered length L is made up of three different length parts/portions—L1, L2, L3.

The length part L2 may be made from the same material as the main body length 52. By reason of the taper of the length part L2, it has slightly more flexibility than the main length 52. The taper angle α1 is preferably in the range of 10-30°.

The length part L3 is made with sufficient rigidity that the distal tip 56 does not collapse so as to pinch the guide wire 12 as when the bent part 44 of the guide wire 12 is encountered. The length part L3 may be made from the same material, such as plastic, that makes up the main body length 52, or another material that is less flexible than that making up the length part L1.

The length part L1 is made from a more flexible material than that making up the main body length 52. As one example, the length part L1 may be made from a rubber material. Accordingly, the length part L1 makes the body 14 locally flexible in a manner that allows a limited and controlled predetermined degree of bending at the distal region of the dilator 10. This bending can be seen most clearly in FIG. 9 wherein the length part L2 is shown slightly bent and the length part L1 more prominently bent to conform to the bent guide wire 12.

The dilator 10 and guide wire 12 are preferably designed to each bend on the order of 20°-30° so as to avoid kinking or breaking of the guide wire 12 while at the same time permitting smooth access by the dilator to the space 38. More specifically, the guide wire 12, where the full thickness of the sleeve 30 surrounds the core 28, preferably bends 20-30° over 1-2 cm. The length part L1 of the dilator 10 has similar bending properties, with some additional bending permitted by the tapered length part L2.

In one exemplary form, the length L3 is on the order of 2-4 mm. The length L1 may be on the order of 2-6 cm, with the entire length L being on the order of 3-8 cm. Substantially the entire length L1 might be made from the more flexible/rubber material.

With the basic teachings in hand, one skilled in the art might change the configuration of the dilator 10 and guide wire 12 to achieve the desired results. What is desired is that the tubular body is locally flexible at its distal region and more rigid away from the distal region so that the surgeon has positive control over the repositioning of the dilator 10 while at the same time retaining the conformability of the distal region to the bent guide wire 12. If the dilator body 14 was highly flexible over more of its length, this positive control aspect would be compromised.

Within the schematic showing of FIG. 2, it is contemplated that the locally flexible portion of the dilator 10 might have a flexibility that is constant or progressively changing along its length, as in the depicted embodiment.

With respect to the guide wire 12, the schematic showing in FIG. 3 is intended to encompass any varying flexibility over the length of the guide wire, with the distal region being more flexible than a location spaced from the distal end of the guide wire towards the proximal end. For example, while an abrupt transitioning between the exposed portion of the core 28 and that surrounded by the sleeve 30 is contemplated, more preferably a transition region is provided, as described above, to make a progressive change in flexibility. Ideally, the wire is designed to bend on the order of 20°-30° over 1-2 cm to match a maximal desired bend of the distal region of the dilator 10.

Figure 9:
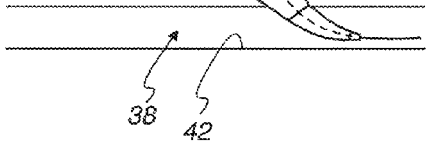
FIG. 9 is a view as in FIG. 8 wherein the dilator is further advanced over the guide wire to conform the dilator to a bent portion of the guide wire.
Figure 10:
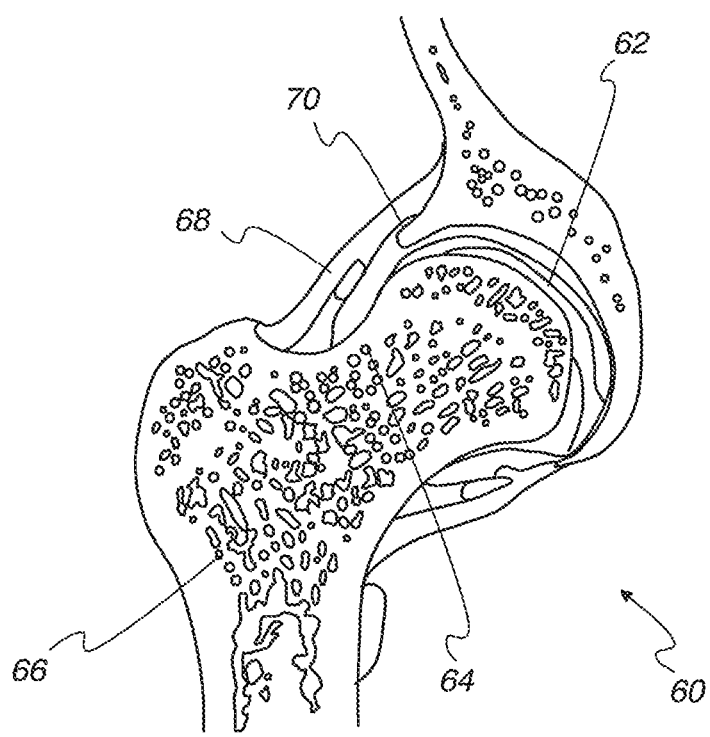
FIG. 10 is a fragmentary view showing a hip joint as one exemplary location at which the inventive dilator and guide wire can be effectively utilized, in this case to direct the guide wire to a desired access site with entry at the femoral head on the hip joint.

In FIG. 10, one specific application, to which the inventive dilator 10 and guide wire 12 are particularly adapted, is shown. This particular application should not be viewed as limiting. In FIG. 10, a hip joint is shown at 60, with access gained to a space 62, typically identified as the femoral-acetabular joint space. According to the invention, access is gained through the region at the neck 64 of the femur 66. Access is gained through the fibrous capsule 68, entering the femoral-acetabular space 62 by direction through the capsule 68 at the femoral neck region and thereafter proceeding past the acetabular labrum 70. The guide wire 12 is required to bend to enter the space 62. Once the guide wire 12 is advanced to the desired access site, the distal end of the dilator 10 is advanced along the guide wire 12 so that the locally flexible length of the body 14 conforms to the bent length of the guide wire 12, as shown in FIG. 9.

In this application, dilators with maximum diameters of 4.76 mm and 6.25 mm were usable effectively with a guide wire having a maximum diameter of 1.5 mm.

The foregoing disclosure of specific embodiments is intended to be illustrative of the broad concepts comprehended by the invention.

The invention claimed is:

1. In combination:
   a) a dilator comprising:
      a tubular body with a length, an internal passage, and proximal and distal ends spaced in a lengthwise direction; and
   b) an elongate guide wire having a length and capable of being received in, and movable in a lengthwise direction within, the internal passage with the dilator and guide wire in operative relationship,
   wherein the tubular body is made from at least first and second different materials, the first material being more flexible than the second material,
   wherein the tubular body has a tapered length at the distal end of the tubular body, the tapered length has a first portion, a second portion, and a third portion, the second portion is between the first and third portions and made from the first material, the first portion is made from the second material, and the third portion is made from a material that is less flexible than the first material,
   wherein the tapered length allows a limited predetermined degree of bending to conform to a curved guide wire shape.

2. The combination according to claim 1 wherein the tapered length is in the range of 3-8 cm.

3. The combination according to claim 1 wherein the tubular body spaced away from the tapered length toward the proximal end is made from a material that is less flexible than the first material to facilitate controlled positioning of the tubular body and conformance of the tapered length to a curved guide wire shape.

4. The combination according to claim 3 wherein the tapered length is in the range of 3-8 cm.

5. The combination according to claim 4 wherein the second portion of the tapered length made from the first material has a length in the range of 2-6 cm.

6. The combination according to claim 3 wherein the first material is rubber.

7. The combination according to claim 6 wherein the second material is plastic.

8. The combination according to claim 3 wherein the third portion defines a tip at a distal end of the tapered length.

9. The combination according to claim 8 wherein the tip is made from plastic.

10. The combination according to claim 3 wherein the guide wire has a distal end and a body comprising a sleeve and a core surrounded by the sleeve and having a portion projecting from the sleeve, the projecting portion of the core defining a distal region of the guide wire that is locally more flexible than a portion of the guide wire where the sleeve surrounds the core.

11. The combination according to claim 3 wherein the guide wire has varying flexibility over the length of the guide wire.

12. The combination according to claim 11 wherein the guide wire has a distal end and the guide wire is more flexible at the distal end of the guide wire than a location spaced from the distal end of the guide wire.

13. The combination according to claim 12 wherein the guide wire has a progressively changing flexibility that increases toward the distal end of the guide wire.

14. A method of placing a dilator in an operative position in a femoral-acetabular joint space, the method comprising the steps of:
   providing the combination as in claim 1 with the guide wire having a distal end;
   directing the distal end of the guide wire into the femoral-acetabular joint space in a manner whereby the guide wire has a bent length; and
   with the guide wire in the internal passage and spaced from the bent length of the guide wire, advancing the distal end of the dilator so that the tapered length of the tubular body engages and conforms to the bent length of the guide wire.

15. The method of placing a dilator according to claim 14 wherein the guide wire has varying flexibility over the length of the guide wire.

16. The method of placing a dilator according to claim 14 wherein the guide wire has a body comprising a sleeve and a core surrounded by the sleeve, a portion of the core projecting from the sleeve and more flexible than a portion of the guide wire where the sleeve surrounds the core, and the bent length is defined by the projecting portion of the core.

* * * * *